US006287837B1

(12) United States Patent
Beaudoin et al.

(10) Patent No.: US 6,287,837 B1
(45) Date of Patent: *Sep. 11, 2001

(54) MAMMALIAN ATP-DIPHOSPHOHYDROLASES AND PROCESS OF PURIFICATION THEREOF

(75) Inventors: Adrien R. Beaudoin, Rock Forest; Jean Sevigny, East Angus, both of (CA)

(73) Assignees: Université de Sherbrooke, Sherbrooke (CA); Beth Israel Deaconess Medical Center, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/930,921

(22) Filed: Jan. 2, 1998

Related U.S. Application Data

(63) Continuation of application No. 08/777,859, filed on Dec. 31, 1996, now Pat. No. 5,798,241, which is a continuation of application No. 08/419,204, filed on Apr. 10, 1995, now abandoned.

(51) Int. Cl.[7] .............................. C12N 11/00; C12N 9/76; C12N 9/14
(52) U.S. Cl. ......................... 435/195; 435/174; 435/177; 435/180
(58) Field of Search .................................. 435/188, 174, 435/177, 180, 195

(56) References Cited

U.S. PATENT DOCUMENTS 5,798,241 * 8/1998 Beaudoin et al. ................... 435/188

FOREIGN PATENT DOCUMENTS

WO 94/02015    3/1994  (WO).

OTHER PUBLICATIONS

Laemmli U.K., 1970, Nature 227:680–685.
Patel et al., 1969, BBA 178:626–629.
Rigbi et al., 1987, Comp. Biochem. Physiol. 87B:567–573.
Bradford M. M., 1976, Anal. Biochem. 72:248–254.
Christoforidis et al., 1995, Eur. J. Biochem. 234:66–74.
Hirota et al., 1987, Thrombosis Res. 45:201–209.
Miura et al., 1987, Thromb. Res. 46:685–696.
Côté et al., 1992, Biochemica and Biophysica Acta 1139:133–142.
Baykov et al., 1988, Anal. Biochem. 171:266–270.
Lebel et al., 1980, J. Biol. Chem. 255:1227–1233.
Laliberté et al., 1982, J. Biol. Chem. 257:3869–3874.
Moodie et al., 1991, Eur. J. Biochem. 202:1209–1215.
Yagi et al., 1989, Eur. J. Biochem. 180(3):509–513.
Côté et al., 1991, Biochim. Biophys. Acta 1078:187–191.
Maliszewski et al., 1994, The Journal of Immunology 153:3574–3583.
Yagi et al., 1992, Chem. Pharm. Bull. 40:2143–2146.

* cited by examiner

Primary Examiner—Herbert J. Lilling
(74) Attorney, Agent, or Firm—Goudreau Gage Dubuc (57) ABSTRACT

The present invention relates to two ATP-diphosphohydrolases (ATPDase enzymes) isolated from bovine aorta and pig pancreas, which enzymes have a molecular weight for their catalytic unit of about 78 and 54 Kilodaltons, respectively. A first process for obtaining a highly purified ATPDase is also an object of the present invention. The process has been successfully applied in the purification of both the pancreatic and the aorta enzymes and is deemed to work in the purification of any ATPDase. For both sources of enzymes, the process allows the specific activity of the enzyme to be increased by at least 10,000 fold when compared to the activity retrieved in the crude cell homogenates. The novel process involves an ion exchange chromatography step, a separation on an affinity column, followed by an electrophoresis under non-denaturing conditions. The two enzymes purified by this process (aortic and pancreatic) are glycosylated and, when deglycosylated, have molecular weights shifted to about 56 and 35 Kdaltons, respectively. Partial amino acid sequences have been obtained for each enzyme. The partial sequences appear highly homologous with a human lymophoid cell activation antigen named CD39. An antibody directed against the porcine pancreatic enzyme cross-reacts with a protein present in endothelial cell lines and in bovine aorta (78 KDa). The high degree of homology of the pancreatic and aortic enzymes with CD39 and their cross-reactivity are indications that both enzymes are related. The pancreatic enzyme completely lacks the first 200 amino acids of CD39, which means the ATPDase activity is comprised between residues 200 and 510 of CD39. Since this is the first time that a sequence is assigned to ATPDase, a second new process for producing ATPDases by recombinant technology can also be used. Therefore, a second new process for producing an ATPDase using the CD39-encoding nucleic acid or part or variant thereof is also described.

22 Claims, 5 Drawing Sheets

MAMMALIAN ATP-DIPHOSPHOHYDROLASES AND PROCESS OF PURIFICATION THEREOF

This is a continuation of application Ser. No. 08/777,859 filed Dec. 31, 1996 now U.S. Pat. No. 5,798,241 which is a continuation of application Ser. No. 08/419,204 filed Apr. 10, 1995 now abandoned.

FIELD OF THE INVENTION

The present invention relates to a process of purification to homogeneity of ATP-diphosphohydrolases involved in numerous nucleotide and nucleoside receptor-mediated physiological functions, namely platelet aggregation, vascular tone, secretory, inflammatory and excretory functions and neurotransmission. These enzymes, which have been particularly obtained from bovine aorta and pig pancreas have been purified and their catalytic unit identified. The partial amino acid sequences of each ATPDase show a high degree of homology with a lymphoid cell activation system named CD39.

BACKGROUND OF THE INVENTION

ATP-diphosphohydrolases (ATPDases) or apyrases (EC 3.6.1.5) have been found in plants, invertebrates and vertebrates. The enzyme catalyses the sequential hydrolysis of the γ- and β-phosphate residues of triphospho- and diphosphonucleosides. These enzymes are generally activated in the presence of divalent cations $Ca^{+2}$ or $Mg^{+2}$ and inhibited by sodium azide. In plants, the enzymes are found in the cytoplasm, in soluble or membrane-associated forms, and are generally more active at acid pH. Their precise function is not known, but there is some evidence that they are involved in the synthesis of carbohydrates. In invertebrates, the enzymes are more active at neutral or alkaline pH. Found mainly in saliva and in salivary glands of hematophagous insects, an antihemostatic role has been demonstrated. In vertebrates, a limited number of studies have already defined a diversity of ATPDases. The catalytic site of these enzymes is generally exposed to extracytoplasmic spaces (ectoenzymes). By their location and kinetic properties, these different types of ATPDases could influence the main systems of the organism, namely vascular and nervous systems. Their specific role in these systems is determined by the presence of purine and pyrimidine receptors which react with triphosphonucleosides and their derivatives at the surface of numerous cell types.

Presence of both ectoATPase and ectoADPase activities in the vascular system has been known for many years, and up until the work of Yagi et al. (1989), they were attributed to two distinct enzymes. The latter purified these activities and showed that in bovine aorta, a single enzyme was responsible for the sequential hydrolysis of ATP and ADP. A mammalian ATPDase had been first described in the pancreas (Lebel et al., 1980) and was further reported in several other tissues. Yagi et al. (1989) proposed that the enzyme from aorta was similar to the previously reported mammalian ATPDase from pancreas and that it was associated with the intima of bovine aorta.

Purification to homogeneity was demonstrated by SDS-polyacrylamide gel electrophoresis (PAGE) and silver staining. The apparent molecular weight of the pure enzyme was estimated at 110 KDa. The existence of the ATPDase in the bovine aorta was corroborated by Côté et al. (1991) who, by showing that identical heat and irradiation-inactivation curves with ATP and ADP as substrates, assigned to the same catalytic site the ATPase and ADPase activities. A comparison of the biochemical properties led Côté et al. supra to propose that the bovine aorta enzyme was different from the pancreas ATPDase. Indeed, the enzymes have different native molecular weights, optimum pH and sensitivities to inhibitors. They proposed to identify pancreas enzyme as type I and the aorta enzyme as type II. In the bovine aorta, the enzyme was found to be associated with smooth muscle cells and endothelial cells and could inhibit ADP-induced platelet aggregation. Côté et al. (1991) further showed that concurrent addition of ATPDase and ATP to platelet-rich plasma resulted in an immediate dose-dependent platelet aggregation caused by the accumulation of ADP, followed by a slow desaggregation attributable to its hydrolysis to AMP. In the absence of ATPDase, ATP did not induce any aggregation while ADP initiate an irreversible aggregation which extent is limited by the ADPase activity of the enzyme. ATPDase also attenuated the aggregation elicited by thrombin and collagen but not by PAF (Platelet Activating Factor), the first two agonists having an effect mediated by platelet ADP release. It was therefore suggested that ATPDase had a dual role in regulating platelet activation. By converting ATP released from damaged vessel cells into ADP, the enzyme induced platelet aggregation at the sites of vascular injury. By converting ADP released from aggregated platelets and/or from hemolyzed red blood cells to AMP, the ATPDase could inhibit or reverse platelet activation, and consequently limit the growth of platelet thrombus at the site of injury. In their attempt to further characterize the aorta ATPDase, the present inventors have developed a new process for producing highly purified ATPDases. They have established a procedure by which its specific activity can be increased over and above the activity of a crude cell preparation by more than 10000-fold. They also discover that the purified enzyme (the catalytic unit) had a molecular weight different from the one previously reported for the native form of the enzyme (190 KD by using the irradiation technique), suggesting that the enzyme may exist in a multimeric form in its native state. Partial amino acid sequences of both bovine aorta and porcine pancreatic ATPases have been obtained.

In a completely different field, Maliszenski et al. (1994) have published the sequence of a human lymphoid cell activation antigen designated CD39. Another group (Christoforidis et al. 1995) described the purification of a human placenta ATPDase of a molecular weight of 82 KDa. Its partial amino acid sequence shows a high degree of homology with CD39.

When the above mentioned partial amino acid sequences were entered in GenBank for verifying the presence of any homologous sequence, complete homology was surprisingly found for some of these fragments with the CD39 gene product. The complete sequences of the ATPDases remain to be obtained. Assuming that CD39 is an up to date unknown ATPDase, a process for producing ATPDases by recombinant technology is now possible, and CD39 can now be used to reduce platelet aggregation and thrombogenicity.

STATEMENT OF THE INVENTION

It is an object of the present invention to provide two ATPDases isolated from bovine aorta and porcine pancreas, which enzymes have a molecular weight for their catalytic unit of about 78 and 54 Kilodaltons, respectively. A novel process for obtaining a highly purified ATPDase is also an object of the present invention. This process has been successfully applied to the purification of both the pancreatic and the aorta enzymes and is deemed to work in the purification of any ATPDase. For both sources of enzymes, the process allows the specific activity of the enzyme to be increased by at least 300 fold when compared to the activity retrieved in the microsomial fraction of these cells as previously reported for an aortic and pancreatic proteins of a native molecular weight of about 190 and 130 KDa, respectively.

The two ATPDases purified to homogeneity were partially sequenced. These sequences have shown striking similarities with a human lymphoid cell activation antigen named CD39 (Maliszenski et al., 1994). Since the molecular weight of CD39 and its glycosylation rate appears to define a human counterpart for the present bovine aortic ATPDase, it is the first time that a sequence is assigned to an ATPDase. A process of producing an ATPDase by recombinant technology is now possible using a host cell expressing the CD39 human protein, its homologous sequences in bovine and porcine species, and variants and parts thereof.

The present invention also relates to the use of CD39 and of the above bovine and porcine homologous proteins for reducing platelet aggregation and thrombogenicity.

DESCRIPTION OF THE PRESENT INVENTION

The research team to which the present inventors belong has already characterized the pig pancreatic ATPDase, and the latter reassessed the properties of the bovine aorta enzyme. They confirmed that the aorta ATPDase was different from its pancreatic counterpart. They have found previously (Côté et al., 1992) that the aorta enzyme (isolated from a microsomal fraction of the cells) had a molecular weight of about 190 kDa in its native state. In their work for extensively purify this enzyme, they found that the highly purified enzyme had a molecular weight on SDS-PAGE of about 78 KDa. Yagi et al. (1989) have already shown that an ATPDase purified to homogeneity had a molecular weight of 110 KDa. After purifying the enzyme by the present method, the 110 kDa band was indeed absent from SDS-PAGE. A unique band migrating of an estimated weight of 78 KDa was rather revealed. The confirmation of the identity of the purified enzyme was achieved by binding FSBA, an ATP analog binding the enzyme, to the separated and blotted enzyme. The use of anti-FSBA antibodies revealed the presence of the bound enzyme and this binding was inhibited with ATP and ADP. The same procedure was applied to confirm the identification of the pancreas ATPDase Type I.

The present process allows the purification of ATPDases to a very high level. In the aorta, the purified enzyme has a specific activity which is increased by at least 300 fold compared with the specific activity of microsomal fraction (already enriched by about 30 fold from the crude cell preparation).

The bovine aorta and porcine pancreatic ATPDases have been partially sequenced, and the sequences have been found to be highly homologous to a human lymphoid cell activation antigen designated CD39 (Maliszenski et al.,op. cit.). The complete sequences of the ATPDases types I and II have not been obtained yet. If one assumes that CD39 gene product is an ATPDase type II, the present invention therefore contemplates the use of CD39 in the reduction of platelet aggregation and of thrombogenicity, as well as a process of making ATPDases using the CD39 sequence, variants or parts thereof (recombinant technology).

The present invention will be described hereinbelow with reference to the following Examples and Figures which purpose is to illustrate rather than to limit the scope of the present invention.

BRIEF DESCRIPTION OF THE FIGURES

FIG. 1 illustrates the protein composition of the bovine aorta ATPDase (type II) at the different purification steps as determined by SDS-PAGE. Electrophoresis was run in a 7–12.5% polyacrylamide gel. Proteins were stained with Coomassie Blue or silver nitrate dye. MW standards: 97.4, 66.2, 45.0, 31.0, 21.5, 14.4 KDa; particulate fraction (part. fract.), 100 µg; DEAE-agarose fraction, 35 µg; Affi-Gel blue fraction, 20 µg; the lower band of activity was cut out from the non-denaturing gel (N.D. gel); sample buffer alone (Control).

EXAMPLE 1

Figure 1:
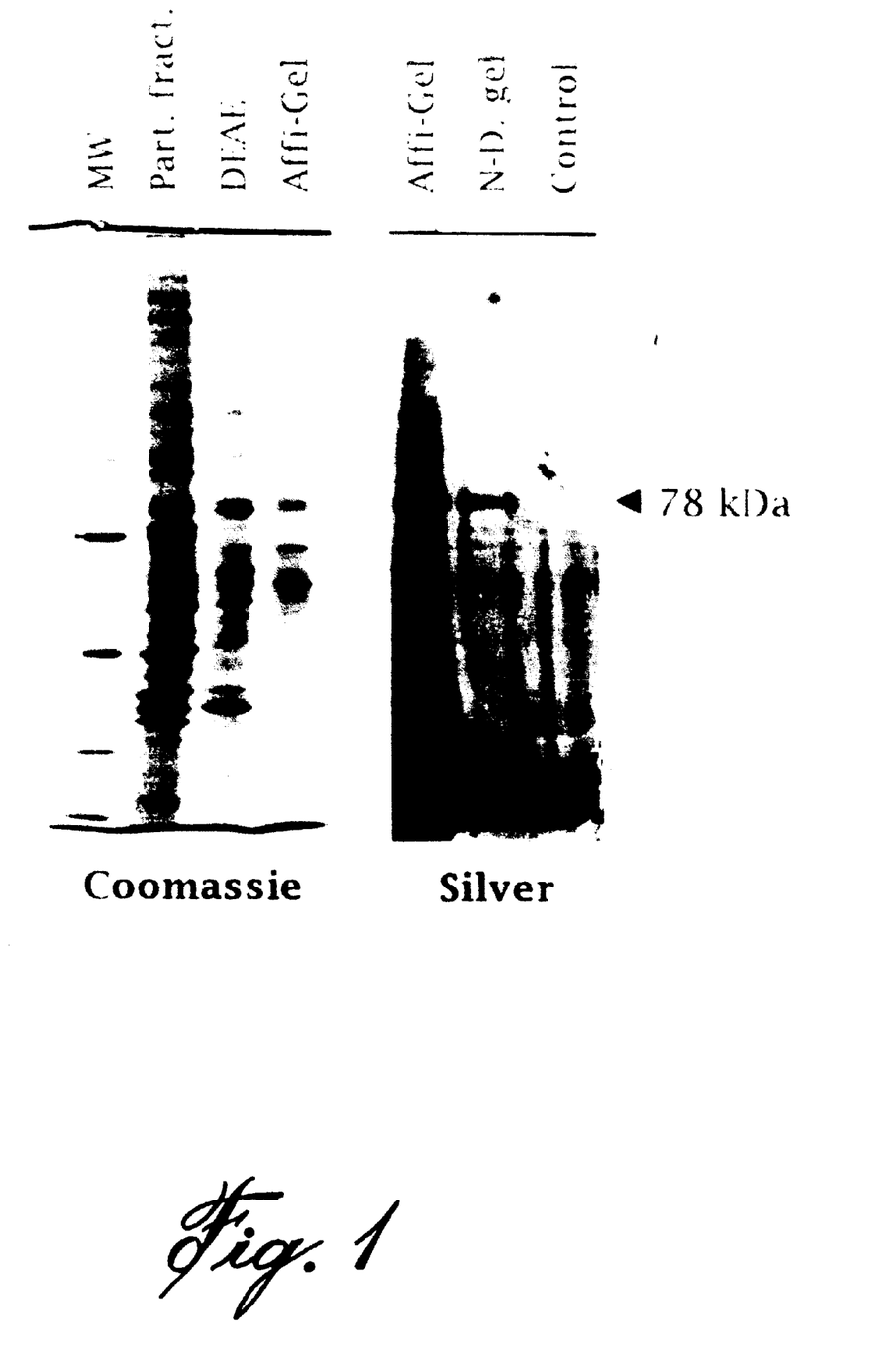

PURIFICATION OF THE ATPDase type II a) Isolation of the particulate (microsomal) fraction from the bovine aorta:

Bovine aorta, obtained from a local slaughterhouse, were kept on ice and processed within one hour after the death of the animals. All steps were carried out at 4° C. The inner layer was stripped out manually, passed through a meat grinder, and homogenized (10%) with a Polytron™ in the following solution: 95 mM NaCl, Soybean Trypsin Inhibitor (20 µg/mL), 0.1 mM Phenylmethyl-sulphonyl-fluoride (PMSF) and 45 mM Tris-HCl pH 7.6. After filtering with cheesecloth, the homogenate was centrifuged at 600 X g for 15 minutes with a Beckman JA-14 centrifuge at 2100 RPM. The supernatant was recovered and centrifuged at 22,000 X g for 90 minutes with the same centrifuge at 12,000 RPM. The resulting pellet was suspended in 0.1 mM PMSF and 1 mM NaHCO$_3$ pH 10.0 with a Potter Elvejehm™ homogenizer at a dilution of 3 to 6 mg of protein per mL. The suspension was loaded on a 40% sucrose cushion and centrifuged at 100,000 X g for 140 minutes with a SW 28 Beckman rotor. The enzyme was recovered on the cushion and kept at 4° C. overnight. This membrane preparation was then suspended in 12 volumes of 0.1 mM PMSF and 1 mM NaHCO$_3$ pH 10.0 and centrifuged at 240,000 X g for 45 minutes in a SW 50.2 Beckman rotor. The pellet was rinsed twice: once with 0.1 mM PMSF and 30 mM Tris-HCl ph 8.0 and once with 2 mM EDTA and 30 mM Tris-HCl pH 8.0. The final pellet was suspended in 7.5% glycerin and 5 mM Tris-HCl ph 8.0 at a concentration >1 mg of protein per mL and frozen at −20° C, or directly solubilized. At this stage, the specific activity of the ATPDase was enriched by about 33 fold.

b) Solubilization and column chromatographies:

The particulate fraction (pf) was solubilized with 0.3% Triton X-100™ and 30 mM Tris-HCl pH 8.0 at a concentration of 1 mg/mL protein and centrifuged at 100,000 X g for 1 hour in a SW 50.2 Beckman rotor. All further steps involving a detergent are practised with Triton X-100, but any similar detergent (a non-ionic detergent) may be used for achieving the purpose of this invention. The supernatant was loaded on an ion exchange column, preferably containing diethylaminoethyl (DEAE), like DEAE-Bio Gel A Agarose™, preequilibrated with 0.1% Triton X-100™, 7.5% glycerin and 10 mM Tris-HCl pH 8.0. The protein was eluted in the same buffer by a NaCl gradient (0.03 to 0.12 M), followed by a 0.1% Triton X-100™ and 2 M NaCl wash. Active fractions were pooled in 0.1X buffer E (5X buffer E: 0.5% Triton X-100™, 960 mM glycine, 125 mM Tris-HCl pH 7.0) and electrodialysed in 15 mL cuvettes by an ISCO™ electro-eluter according to the following technique: 1X buffer E was loaded in the apparatus and a 15 mA current was applied per cuvette. The 1X buffer E was changed 4 times at 50 minute intervals. The dialysate was equilibrated at pH 5.9 with 200 mM histidine adjusted to pH 4.0 with HCl (about 20 mM final) and loaded on an Affi-Gel™ blue column preequilibrated with 0.07% Triton X-100™, 7.5% glycerin, 30 mM histidine and 30 mM Tris-HCl pH 5.9. Proteins were eluted by a linear gradient from 100% buffer A to 100% buffer B (buffer A (80 ml): 0.07% Triton X-100™, 7.5% glycerin and 10 mM Tris-HCl pH 6.5; buffer B (80 ml): 1M NaCl, 0.07% Triton X-100™, 7.5% glycerin and 10 mM Tris-HCl pH 7.5), followed by a 1M NaCl, 0.1% Triton X-100™, 100 mM Tris-HCl pH 8.5 wash. The active fraction was dialysed against 0.05% Triton X-100™, 1 mM Tris-HCl pH 8.0, concentrated on a 1 ml DEAE-agarose column as described above, eluted in 0.4 M NaCl, 0.07% Triton X-100™, 10 mM Tris-HCl pH 8.0 and dialysed against distilled water.

c) Separation by polyacrylamide gel electrophoresis (PAGE) under non-denaturing conditions:

This type of gel allows for separating proteins upon their molecular weight and electrical charge while preserving their activity in such a way that this activity can be measured after migration. Two polyacrylamide preparations were poured between two glass plates to form a gradient and polymerized. The 4% acrylamide solution was composed of: 4.5 mL of separating buffer (Tris 1.5 M pH 8.8+0.4% Triton X-100™), 2.5 mL acrylamide 30%, 180 µL Na deoxycholate 10%, water up to 18 mL, 60 µL APS 10% and 7 µL TEMED. The 7.5% acrylamide solution was composed of the same ingredients except for the volume of acrylamide: 4.5 mL. A stacking gel was extemporaneously prepared and poured at the top of the separating gel, the stacking gel was composed of: 2.5 mL of stacking buffer (Tris-base 0.5 M pH 6.8), 6.1 mL of water, 1.34 acrylamide 30%, 0.1 mL Na deoxycholate 10%, 0.1 mL Triton X-1007™, 50 µL APS 10% and 10 µL TEMED. Wells are formed in this layer during polymerization. Two volumes of the sample obtained after DEAE-agarose or Affigel Blue columns were added to one volume of sample buffer of the following composition to obtain about 100 µg proteins: 0.07% (v/v) Triton X-100™, 1.5% (w/v) Na deoxycholate, 10% glycerol, 65 mM Tris-base and 0.005% bromophenol blue. The suspended sample was allowed to stand 10 minutes on ice and centrifuged. The supernatant was loaded on gel. The proteins were migrated at 4° C. at a 20 mAmp power in reservoir buffer (0.1% Triton X-100, 0.1% sodium deoxycholate, 192 mM glycine and 25 mM Tris pH 8.3). For revealing activity in the separated bands, the latter were placed in a dosage buffer (Tris-base 66.7 mM, imidazole 66.7 mM, CaCl$_2$ 10 mM, pH 7.5). After preliminary incubation for 30 minutes at 37° C., the substrate (ADP or ATP) 5 mM was added. After 2 to 10 minute incubation, a white calcium phosphate precipitate significative of ATP diphosphohydrolase activity is formed. Three bands are seen for the aorta enzyme and one for the pancreas (these bands were all revealed on gel by silver overstaining). For further characterization, the most active band was loaded on an SDS-PAGE according to Laemmli (1970) and a single band appeared on the gel after silver nitrate staining, which is indicative of an enzyme purification to homogeneity after the non-denaturing gel. FIG. 1 shows the high sensitivity of detection conferred by the use of silver staining compared to a conventional Coomassie blue staining (see lanes 4 and 5). The active band purified from the gel has a molecular weight of 78 KDa when migrated on SDS-PAGE.

d) ATPDase assays during chromatographic steps:

Enzyme activity was determined at 37° C. ins the following incubation medium: So mM Tris-imidazole (pH 7.5), 8 MM CaCl$_2$ and 0.2 mM substrate (ATP or ADP). Phosphorus was measured by the malachite green method according to Baykov et al. (1988). One unit of enzyme corresponds to the liberation of 1 µmol of phosphate per minute per mg of protein at 37° C. Proteins were estimated by the technique of Bradford (1976).

The ATPDase activity retrieved in isolated fractions are summarized in the following Table:

TABLE 1

ATPDase purification of the bovine aorta ATPDase type II

Figure 2:
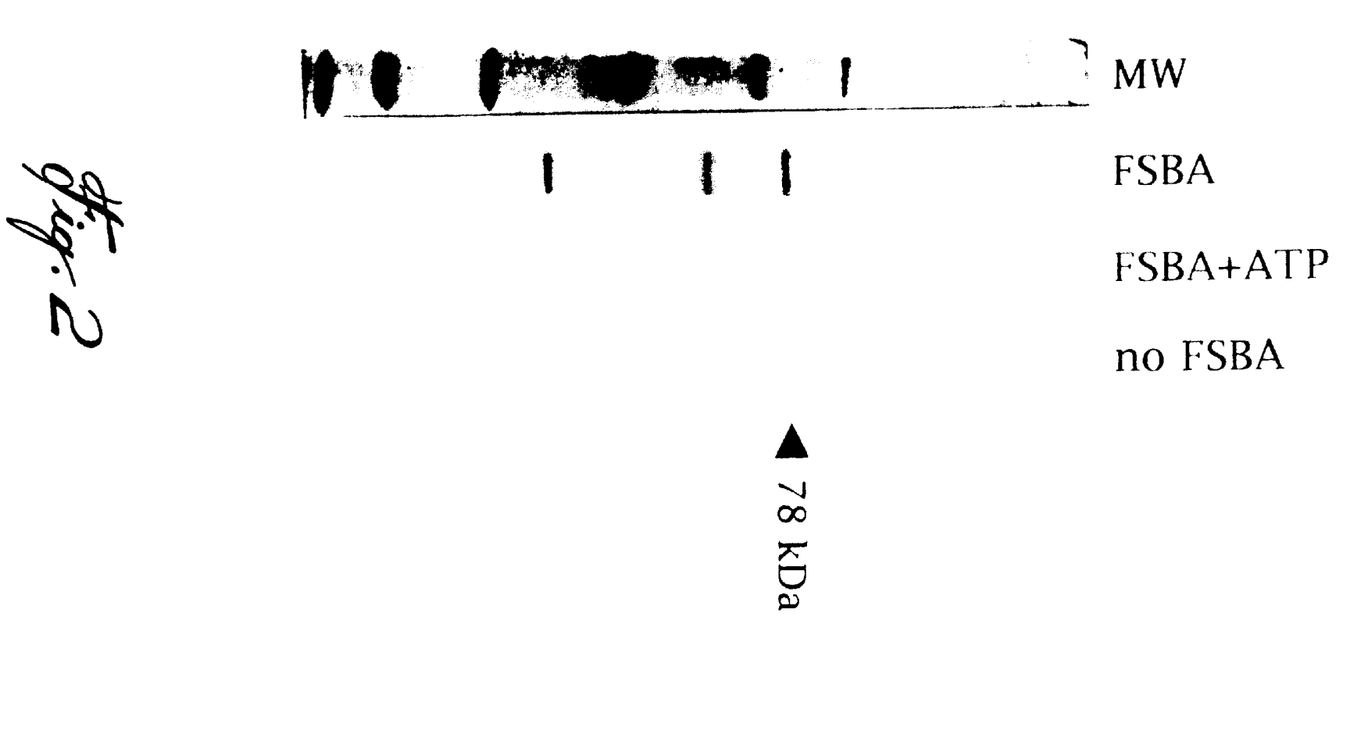
FIG. 2 illustrates a Western blot of FBSA labelled protein (ATPDase type II) isolated from Affi-Gel blue column. Labelled proteins were separated on a 8–13.5% gradient gel by SDS-PAGE, transferred to Immobilon-P membrane, incubated with a rabbit antibody anti-FBSA (1:10,000) and detected by a secondary antibody conjugated to alkaline phosphatase (1:6,000). Twenty µg of protein from Affi-Gel blue column fraction was used for the assays: incubation with FBSA (FBSA); incubation with FBSA with competing Ca-ATP (FBSA+ATP); incubation without FBSA (no FBSA). MW standards are the same as in FIG. 1.
Figure 3:
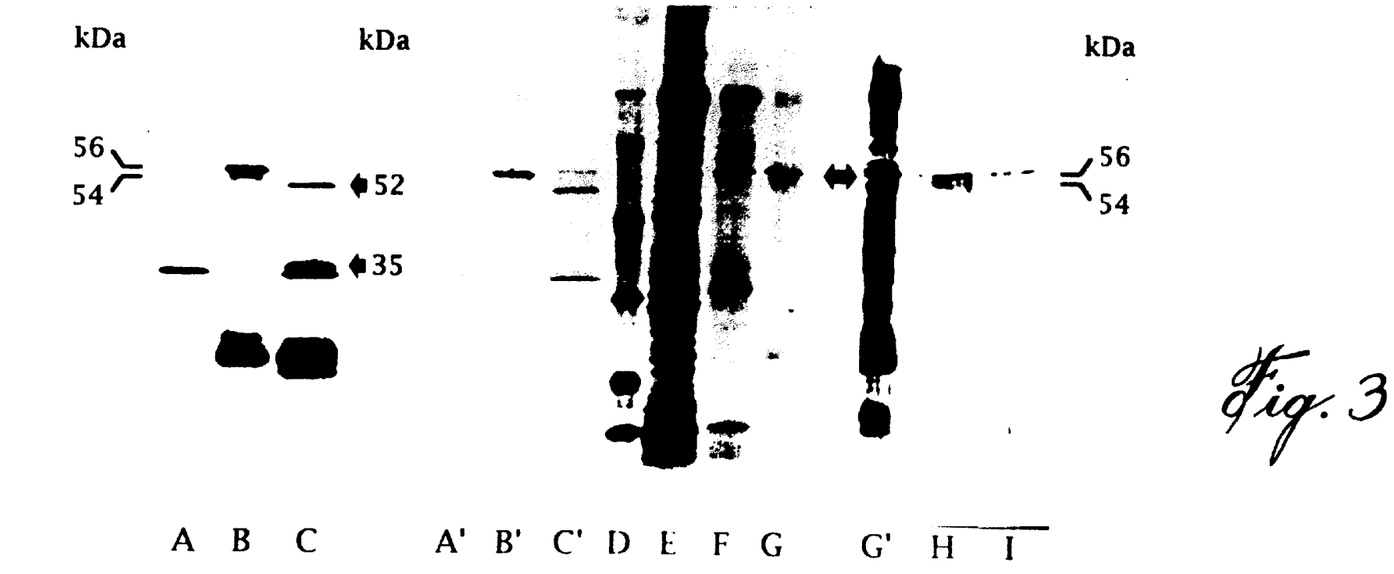
FIG. 3 illustrates the SDS-PAGE protein patterns at the different steps of the purification procedure and after N-glycosidase F digestion of the Affi-Gel blue fraction. Protein samples were fractionated on a 8–13.5% polyacrylamide gradient. A) One unit of N-glycosidase F (silver nitrate stain); B) Six µg from the Affi-Gel blue fraction incubated for 12 h without N-glycosidase F (silver nitrate stain); C) Idem as B with 1 unit of N-glycosidase F (silver nitrate stain); A') Same as A (Coomassie blue stain); B') Same as B (Coomassie blue stain); C') Same as C (Coomassie blue stain); D) MW standards: 97.4, 66.2, 45.0, 31.0, 21.5, 14.4 kDa (Coomassie blue stain), E) ZGM (zymogen granule membrane), 60 µg (Coomassie blue stain); F) Active fraction from DEAE-agarose column, 25 µg (Coomassie blue stain); G) Active fraction from Affi-Gel blue column, 6 µg (Coomassie blue stain); GI) Same as G (silver nitrate overstain); H) Activity band located after PAGE under non-denaturing conditions (silver nitrate overstain); I) Control, band located just above the activity band after PAGE under non-denaturing conditions (silver nitrate overstain).
Figure 4:
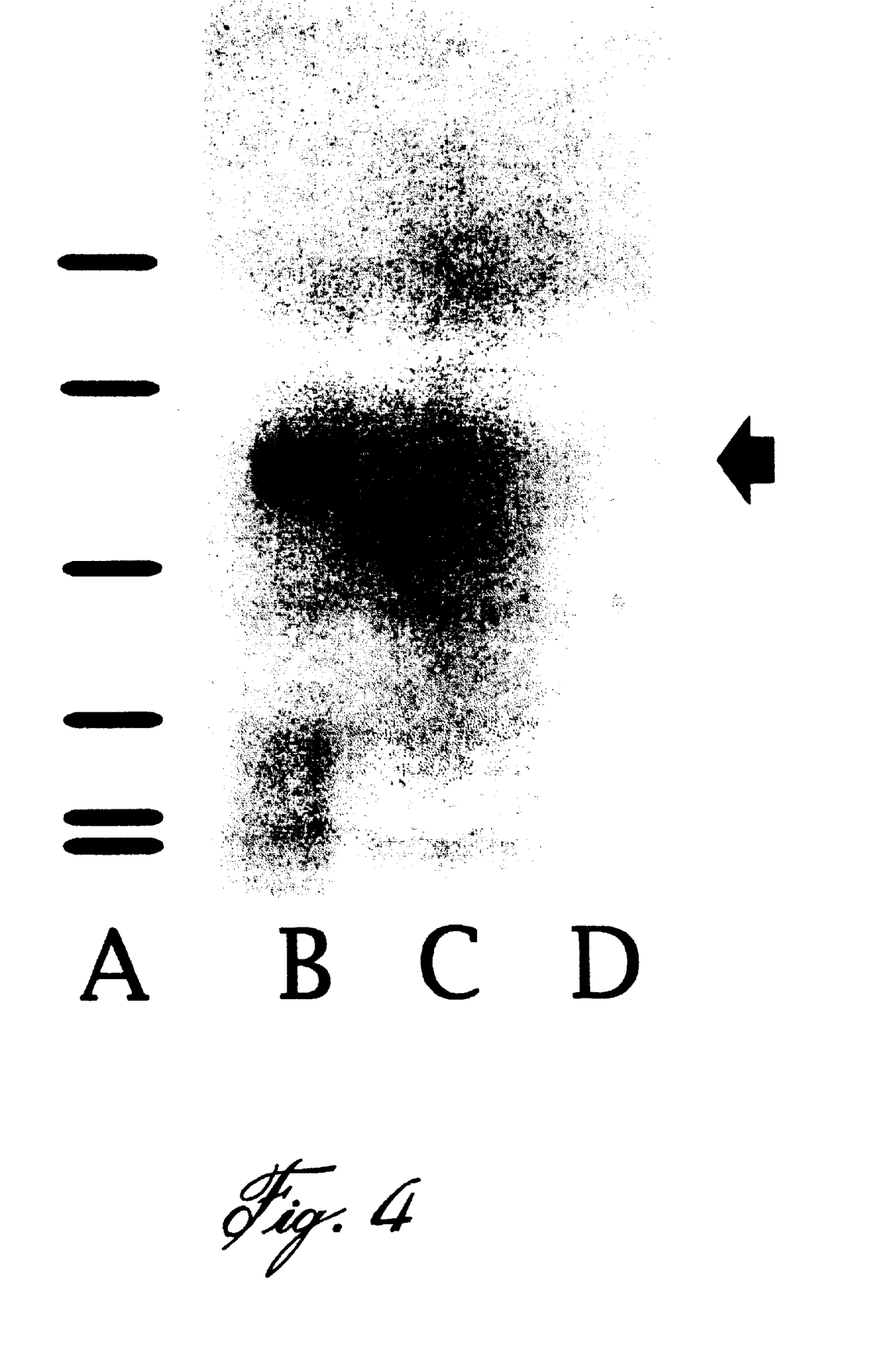
FIG. 4 shows a Western blot of FSBA labelled samples of the pancreatic enzyme type I fraction. Labelled sample were loaded on a 7–12t polyacrylamide SDS-gel, transferred to Immobilon-P membrane, incubated with the rabbit antibody anti-FSBA and detected by a secondary antibody conjugated to alkaline phosphatase. Six µg of Affi-Gel blue column were used in lanes B), C) and D). A) MW standards: 97.4, 66.2, 45.0, 31.0, 21.5, 14.4 kDa; B) FSBA; C) FSBA+competing ADP; D) No labelling.

| Step | Total protein mg | Total activity units | Specific activity units/mg | Yield % | Purification factor -fold | Hydrolysis rate ATP/ADP |
|---|---|---|---|---|---|---|
| Particulate fraction (pf) | 293 | 263 | 0.9 | — | (33)* | 1.5 |
| pf + Triton X-100 | 293 | 117 | 0.4 | 100 | 1 | 1.4 |
| 100,000 g supernatant of solubilized pf | 186 | 91.2 | 0.5 | 78 | 1.2 | 1.3 |
| DEAE column | 15.1 | 72.2 | 4.8 | 62 | 11.9 | 1.1 |
| Affi-Gel blue column | 2.76 | 57.8 | 21 | 49 | 53 | 1.1 |
| Con A | 0.61 | 33.5 | 55 | 29 | 138 | 1.1 | e) Confirmation of the identity of ATPDase:

The fraction eluted from Affi-gel was labelled with 5'-p-fluorosulfonylbenzoyl adenosine (FBSA), a marker which forms covalent bonds with adenosine-binding proteins. FSBA blocked the enzyme activity and excess of ATP or of ADP prevents this effect. In addition, FSBA efficiently bound the purified enzyme, as monitored by a Western blot technique using an antibody directed to FSBA, which binding is prevented in the presence of ATP (see FIG. 2) or ADP (data not shown).

The results obtained on SDS-PAGE shows that the enzyme was purified to homogeneity when using the successive steps of solubilization of the particulate fraction, first purification on an ion exchange column, second purification on an affinity column and third purification on non-denaturing electrophoretic conditions. The Affigel Blue column did not achieve purification to homogeneity but allowed a much higher recovery then the 5' AMP-Sepharose™ used by Yagi et al. (about 7 fold higher). Moreover, the use of the Affigel column and the non-denaturing gel allowed us to purify an enzyme that is different from the one disclosed by Yagi.

f) ATPDases are glycosylated proteins:

Purification on Concanavalin A column: Further purification of the Afti-Gel blue fraction of aorta enzyme was also obtained with Con A agarose column. Briefly, Con A (4 ml beads) and the protein sample from the Affi-Gel blue column were preequilibrated with 0.05% Triton X-100, 100 mM NaCl, 1 mM CaCl$_2$, 1 mM MnCl$_2$ and 20 mM PIPES, pH 6.8, at room temperature. The protein sample was passed through the column at a flow rate of 3 ml/h, 40 ml of the preequilibration buffer was then added to wash the unbound materials at a flow rate of 10 ml/h. The activity was eluted with 20 ml of 0.5 M Me-α-D-mannopyranoside diluted in the preequilibration buffer. The purified sample was dialysed and concentrated on a mini-DEAE column as described above.

Precipitation of ATPDase activity with lectin-agarose:

Four lectins conjugated to agarose were tried: Con A, WGA, Soybean agglutinin and UEA. Experiments were carried out at room temperature for Con A, and at 4° C. for the other agglutinins. One hundred μl of each 50% slurry were put in a microcentrifuge tube and washed 4 times with buffer A: 0.05% Triton X-100, 100 mM NaCl and 20 mM PIPES pH 6.8. In the case of Con A, 1 mM CaCl$_2$ and 1 mM MnCl$_2$ were added to this buffer. Twenty μg of ATPDase purified from the Affi-Gel blue column, equilibrated in buffer A, were added to the lectin-agarose beads and rocked for 45 min, then centrifuged for 1 min. The supernatant was kept and the beads were washed 3 times with 1 ml buffer A. Protein bound to the lectins was eluted with 150 μl of 500 mM of the appropriate sugar in buffer A, rocked for 30 min and centrifuged. The elution step was repeated once and the 2 eluates were pooled. The sugar used to eluate proteins from Con A, WGA, Soybean and UEA were Me-α-D-mannopyranoside, D-GlcNAc, D-GalNAc and L-Fuc respectively.

TABLE 2

ATPase binding to lectins

| Lectin-agarose | Fractions | Relative ADPase activity | Presence of the 78 kDa band on SDS-PAGE | Sugar specificity |
|---|---|---|---|---|
| Con A | Supernatant | 5% | traces | Mannose, |
|  | Bound | 95% |  | Glucose |
|  | Eluted | 62% | + |  |
| WGA | Supernatant | 5% | traces | GlcNAc, NeuNAc, |
|  | Bound | 95% |  | Mannose structure § |
|  | Eluted | 69% | + | Sialic acid § |
| Soybean | Supernatant | 100% | + | GalNAc |
|  | Bound | 0% |  |  |
|  | Eluted | 0% | − |  |
| UEA | Supernatant | 100% | + | Fucose |
|  | Bound | 0% |  |  |
|  | Eluted | 0% | − |  |

Only WGA bound the ATPDase type II as for Con A. ATPDase binding to these two lectins is indicative of a specificity for the sugars glucose and/or mannose and/or GlcNAc (Glucosamine-N-Acetyl) and/or NeuNAc (Neuraminic-N-Acetyl).

The deglycosylated form had a molecular weight of about 56 KDa, which suggests that about 5 to 11 glycosyl chains are present on the 78 KDa protein (assuming that a glycosyl group may have a molecular weight of 2 to 4 KDa).

EXAMPLE 2

PURIFICATION OF THE ATPDase type I

The procedure described in Example 1 has been followed for purifying the pancreatic ATPDase type I enzyme, starting from the zymogen granule membrane of pig pancreas.

In deglycosylation experiments, the molecular weight of the catalytic unit has been shown to be shifted from 54 to 35 KDa. Therefore, the chemical procedure exemplified above is deemed to apply to the purification of ATPDases in general.

h) Level of enrichment:

The level of enrichment is determined from the data shown in Table 1 for aorta ATPDase type II and from the following Table 3 obtained for pancreatic ATPDase type I.

From the crude cell preparation to the Affigel Blue column, the enzymes of both pancreatic and aorta sources were purified to at least a 1600 fold level (see Tables 1 and 3. After the non-denaturing gel, the quantity of proteins falls under the detection level of the method used, which renders difficult the calculation of a specific activity. However, one can roughly estimate the process to reach about a 10 thousand fold purification, as judged by the density of the ATPDase reaction band relative to other proteins on the non-denaturing electrophoretic gel.

Referring to Table 1, the lectin-binding step is not considered properly as an essential step of the purification process. This step has been added to show that the aorta ATPDase is a glycoprotein which, when deglycosylated, shifts from a molecular weight of 78 KDa to a molecular of 56 KDa (representing the proteic backbone). Since the lectin-binding step does not achieve the obtention of a pure protein, the most convenient way to obtain a pure protein is to submit the crude cell preparation sequentially to the ion exchange chromatography, the Affigel Blue chromatography and to non-denaturing gel electrophoresis. The identity of the protein is then confirmed by ATP-labelling with FSBA.

EXAMPLE 3

Partial amino acid sequences

CNBr digests have been obtained from the purified bovine aorta and porcine pancreatic ATPDases. The sequences of the digests are as follows:

|  | SEQ. ID. NO.: |
|---|---|
| Bovine aorta ATPDase: | |
| Glu Thr Pro Val Tyr Leu Gly Ala Thr Ala Gly<br>　　　　　　　5　　　　　　　　10 | 3 |
| Leu Leu Arg Met Glu<br>　　　　　5 | 4 |
| Ala Asp Lys Ile Leu Ala Asn Xaa Val Ala<br>　　　　　　5　　　　　　　10 | 5 |
| Ser Ser Ile | 5 |
| Tyr Pro Phe Asp Phe Gln Gly Ala Arg Ile<br>　　　　　　5　　　　　　　10 | 6 |

|  | SEQ. ID. NO.: |
|---|---|
| Porcine pancreatic ATPDase: | |
| Lys Ser Asp Thr Gln Glu Thr Tyr Gly Ala<br>　　　　　　5　　　　　　　10 | |
| Leu Asp Leu Gly Gly Ala Ser Thr Gln Val<br>　　　　　15　　　　　　　20 | 7 |

When compared to the sequence which accession number is G2345 (CD39 gene product; Maliszenski et al. 1994), the above partial sequences show a very high degree of homology. The following differences are however found with the CD39 sequence:

In the porcine pancreatic enzyme, $Gln^{202}$ is changed to Lys, the $Asn^{204}$ is changed to Asp, $Asn^{205}$ is changed to Thr.

In the bovine aortic enzyme, $Arg^{141}$ is changed to Lys, $Val^{148}$ is changed to Ile, $Asp^{150}$ is changed to Ala, $Gln^{153}$ is changed to Ala, $Arg^{154}$ is changed to Ser, and $Leu^{156}$ is changed to Ile.

The human CD39 has a predicted molecular weight of 57 KDa, while the apparent molecular of this protein is 78KDa on SDS-PAGE.

Both ATPDases type I and II share a high degree of homology with CD39 for the compared sequenced fragments. CD39 appears to be a human enzyme corresponding to the bovine aortic ATPDase. It is worthwhile noting that the first N-terminal 200 amino acids of CD39 are absent from the ATPDase type I (pancreatic enzyme). This suggests that the active site of ATPDases is located between the residues 200–510 of CD39 and that part of CD39 is sufficient to provide this activity. It is further worthwhile noting that exact correspondence between the two ATPDases of this invention and the already described ATPDases cannot be established. The human placenta ATPDase (Christoforidis et al. 1995) has a molecular weight of 82KDa while CD39 (also of human origin) has a molecular weight of 78KDa. Due to the differences found in diverse tissues of the same species, extrapolation cannot be done to the effect that the bovine aorta enzyme of this invention is one of the already described enzymes. The obtained partial amino acid sequences indeed already shown differences of sequences which may affect some of the physico-chemical properties of the claimed enzymes when compared to their human counterparts (some of the above-observed substitutions are not conservative ones; the net charge of the enzymes may not be the same and the substituted amino acids may change the behaviour of the enzymes (optimum pH, sensitivity towards inhibitors, etc . . .).

Cross-reactivity between ATPDases I and II:

Antibodies were produced in rabbits against the following amino acid sequence which is common to ATPDase I and CD39:

|  | SEQ. ID. NO.: |
|---|---|
| Lys Ser Asp Thr Gln Glu Thr Tyr Gly Ala<br>　　　　　　5　　　　　　　10 | |
| Leu Asp Leu Gly Gly Ala<br>　　　　　15 | 8 |

Figure 5:
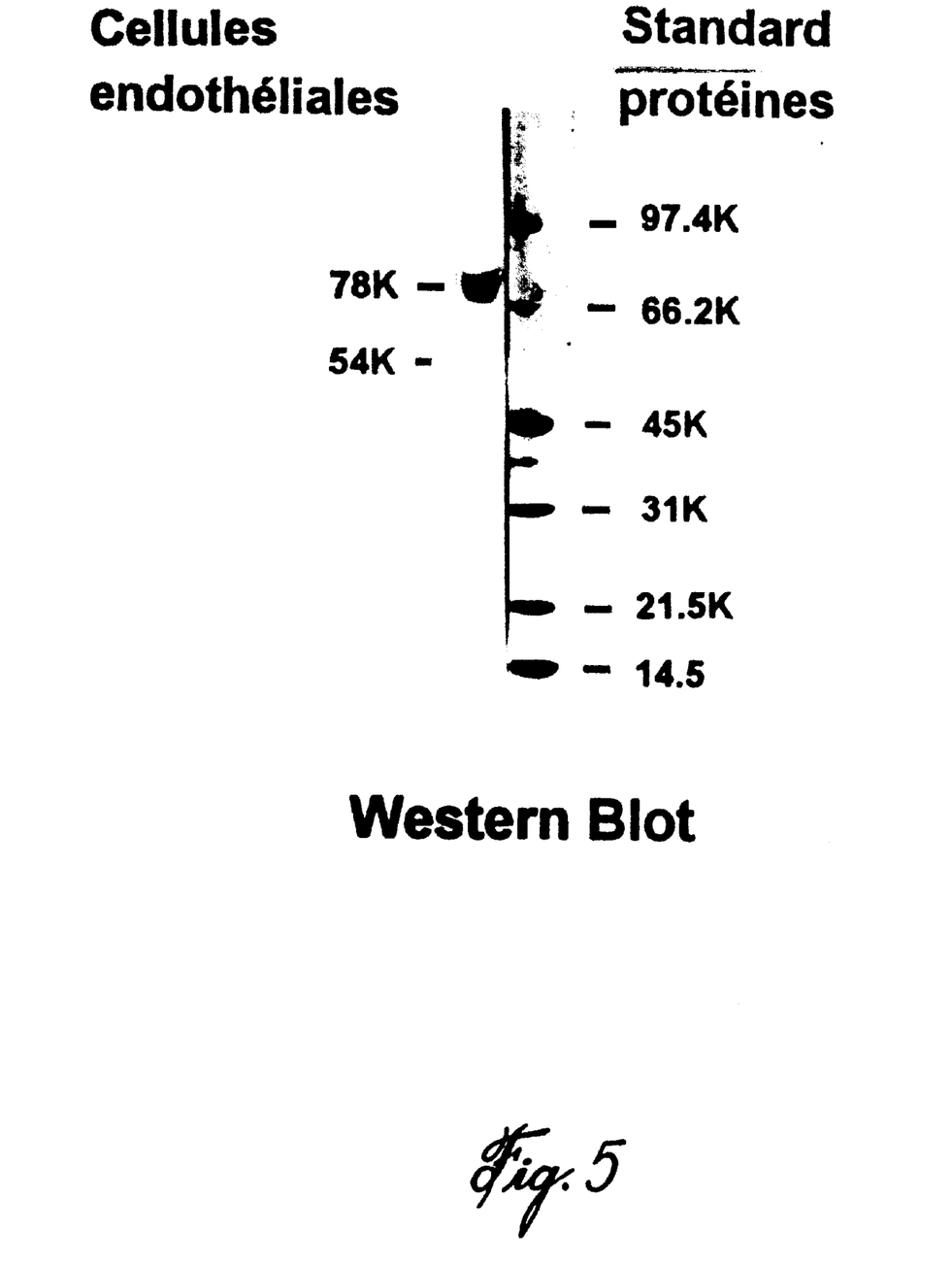
FIG. 5 shows a Western blot of human endothelial cell extracts labelled with an antibody directed against a fragment common to ATPDase type I and CD39. The ATPDase type II (78KDa) is clearly detected as well as low amounts of ATPDase type I (54KDa).

FIG. 5 shows that these antibodies reacted positively with a 78KDa protein present in endothelial extracts of human sources. They also reacted with a protein of 78 KDa of a bovine aorta extract (data not shown). This is an indication that ATPDases I and II share homology of sequence, and that the latter comprises the peptidic sequence of SEQ. ID. No.: 8 or a variant thereof.

A type I ATPDase appears to be present in low amounts in endothelial cells as shown by the detection of a faint band corresponding to this protein (54KDa) in FIG. 5.

CONCLUSIONS:

Considering that the ATPDase has an antihemostatic role in the saliva of blood-feeding insects and leeches (Rigbi et al., 1987);

considering that Côteé et al. (1992) have demonstrated bovine ATPDase type II has platelet anti-aggregant properties by converting ADP to AMP;

considering the low Km of the aorta type II enzyme ($\mu$M), the optimum pH of catalysis pH 7.5–8.0, its localization at the surface of endothelial and smooth muscle cells of blood vessels (Côté et al., 1992);

considering that the purified enzyme keeps its original characteristics;

it sounds predictable that the aorta enzyme produced in the present invention can be introduced in the circulatory system of mammalians to reduce platelet aggregation and thrombogenicity.

Furthermore, considering that a crude microsomal bovine ATPDase type II fraction has been successfully conjugated to agarose and that the conjugate could reduce ADP induced platelet aggregation (Hirota et al., 1987);

considering that a semi-purified plant ATPDase has been successfully coupled to the following matrices: CM-cellulose, copolymers of L-alanine and L-glutamic acid, polyaspartic acid, polygalacturonic acid, Elvacite 2008™ (methyl methacrylate) and ethylene-maleic acid co-polymer (Patel et al., 1969);

we propose that the purified ATPDase type II can be coupled to artificial polymers/biomaterials to reduce thrombogenicity (platelet aggregation).

Therefore, pharmaceutical compositions for use in the reduction of platelet aggregation and thrombogenicity are under the scope of the invention. These compositions should contain, as an active ingredient, the ATPDase type II of this invention combined to an acceptable carrier without excluding any form or formulation of such compositions. Finally, considering that the sequenced CD39 appears to correspond to a human counterpart of the bovine ATPDase type II enzyme of this invention, the use of CD39 or variants or a part thereof for reducing platelet aggregation and thrombogenicity is also part of this invention.

A new process for producing an ATPDase comprising the steps of:

obtaining a host which comprises a nucleic acid encoding a protein having the amino acid sequence defined in SEQ. ID. NO.: 1, or a variant thereof, or a part thereof, said variant or part being capable of converting ATP to ADP and ADP to AMP;

culturing said host in a culture medium supporting the growth of said host and the expression of said nucleic acid;

recovering the ATP diphosphohydrolase from the culture medium or from said host; and purifying the ATP diphosphohydrolase is also part of the invention. Preferably the nucleic acid is the one defined in SEQ ID NO.: 2, or a part or a variant thereof, which part or variant is capable of producing an ATP diphosphohydrolase.

The present invention has been described hereinabove; it will become apparent to the skilled reader that variations could be brought thereto without departing from the teachings of the present disclosure. Such variations are under the scope of this invention.

TABLE 3

ATPDase purification

| Steps | Total protein mg | Total activity units | Specific activity (ATP) units/mg | Yield % | Purification factor fold | Hydrolysis rates ATP/ADP |
|---|---|---|---|---|---|---|
| ZGM | 20.0 | 60.8 | 3.0 | — | (160)* | 1.3 |
| ZGM + Triton X-100 | 20.0 | 40.6 | 2.0 | 100 | 1 | 1.3 |
| 100,000 g supernatant of solubilized ZGM | 17.6 | 37.0 | 2.1 | 91 | 1.1 | 1.3 |
| DEAE column | 3.5 | 28.8 | 8.3 | 71 | 4.2 | 1.3 |
| Affi-Gel blue column | 0.31 | 13.8 | 45 | 34 | 23 | 1.3 |

Results of one out of three preparations is presented. Determinations were carried out in triplicate.
*Laliberté et al. showed a 160 fold purification for the ZGM as compared to the homogenate using ADP as the substrate.

BIBLIOGRAPHY:

Baykov et al. (1988). Anal. Biochem. 171: 266–270.
Bradford, M (1976). Anal. Biochem. 72: 248–254.
Côté et al. (1991). BBA 1078: 187–191.
Côté et al. (1992). BBA 1139: 133–142.
Christoforidis et al. (1995), Eur. J. Biochem. 234: 66–74.
Hirota et al. (1987). Thrombosis Res. 45: 201–209.
Laemmli (1970). Nature 227: 680–685.
Lebel et al. (1980). J. Biol. Chem. 255: 1227–1233.
Maliszenski et al. (1994). J. Immunol. : 3574–3583
Patel et al. (1969). BBA 178: 626–629.
Rigbi et al. (1987). Comp. Biochem. Physiol. 87B: 567–573.
Yagi et al. (1989). Eur. J. Biochem. 180: 509–513.

What is claimed is:

1. An isolated and purified ATP diphosphohydrolase obtainable from a mammalian tissue characterized by the following physico-chemical properties:
   a catalytic unit of molecular weight on denaturing polyacrylamide gel electrophoresis of about 78 KDa;
   a deglycosylated form of said catalytic unit of molecular weight on SDS-PAGE of about 56 KDa; and characterized in that it comprises at least one of the amino acid sequences selected from the group consisting of:
   a) SEQ ID NO:1;
   b) SEQ ID NO:3;
   c) SEQ ID NO:4;
   d) SEQ ID NO:5;
   e) SEQ ID NO:6; and
   f) SEQ ID NO:8.

2. A process for purifying an ATP-diphosphohydrolase enzyme from a tissue capable to convert ATP to ADP and ADP to AMP which comprises:
   a) obtaining a subcellular microsomal fraction from an homogenate of said tissue;
   b) solubilizing said microsomal fraction in the presence of a non-ionic detergent;
   c) centrifuging said solubilized microsomal fraction to obtain a supernatant containing said enzyme;
   d) submitting said supernatant to an ion-exchange chromatography to obtain a first enzyme eluate;
   e) submitting said first eluate to an affinity column chromatography to obtain a second enzyme eluate; and
   f) submitting said second eluate to a separation step on a non-denaturing gel electrophoresis to recover said enzyme free of any contaminant, the presence of said contaminant being monitored by overstaining said gel in a silver nitrate dye or Coomassie Blue dye;
   whereby an isolated and purified ATP diphosphohydrolase according to claim 1 is obtained.

3. A process according to claim 2 wherein said ion exchange chromatography is achieved on a column containing Diethylaminoethyl (DEAE).

4. A process according to claim 3 wherein said column is a DEAE agarose column.

5. A process according to claim 2, wherein an aliquot of said enzyme is further submitted after step f) to a polyacrylamide gel electrophoresis under denaturing conditions to verify its homogeneity and to obtain its apparent molecular weight.

6. A process according to claim 2 wherein said enzyme is obtained from a bovine aortic intima layer and has an apparent molecular weight of about 78 Kilodaltons.

7. A process according to claim 6 herein, between steps e) and f), a step of deglycosylation is included, and whereby the apparent molecular weight is shifted from 78 to 56 KDa.

8. A method for reducing platelet aggregation and thrombogenicity comprising an administration of the ATP diphosphohydrolase of claim 1.

9. A method for reducing platelet aggregation and thrombogenicity comprising an administration of an ATP diphosphohydrolase having the amino acid sequence defined in SEQ ID NO:1.

10. A composition for reducing platelet aggregation and thrombogenicity which comprises as an active ingredient the ATP diphosphohydrolase of claim 1, together with an acceptable pharmaceutical carrier.

11. An aggregation and thrombogenicity reducing composition, which comprises as an active ingredient the mammalian ATP diphosphohydrolase of claim 1 together with a pharmaceutically acceptable.

12. A composition for converting ATP into ADP and/or ADP into AMP, which comprises as an active ingredient the mammalian ATP diphosphohydrolase of claim 1 together with a pharmaceutically acceptable carrier..

13. A process for purifying an ATP diphosphohydrolase enzyme which can convert ATP to ADP and/or ADP to AMP, said process comprising:
   a) separating a crude fraction of said enzyme from contaminating material by centrifugation;
   b) submitting said enzyme of a to at least one of ion-exchange chromatography and affinity column chromatography to obtain a purified enzyme eluate;

whereby an isolated and purified ATP diphosphohydrolase according to claim 1 is obtained.

14. The process of claim 13, wherein said crude fraction is incubated with a non-ionic detergent, prior to centrifugation.

15. The process of claim 14, wherein said enzyme of a) is submitted to at least one round of ion-exchange chromatography to yield a first enzyme eluate, and said first enzyme eluate is submitted to at least one round of affinity chromatography, to yield a second enzyme eluate.

16. The process of claim 15, wherein said second enzyme eluate is electrophoresed on a non-denaturing get, thereby recovering substantially pure ATP diphosphohydrolase, and wherein a presence of contaminants in said substantially pure ATP diphosphohydrolase can be monitored by overstaining said non-denaturing gel in a silver nitrate dye or Coomassie Blue dye.

17. The process of claim 16, wherein said ion exchange chromatography is achieved on a Diethylaminoethyl (DEAE) column.

18. The process of claim 17, wherein said column is a DEAE agarose column.

19. The process of claim 13, wherein said enzyme is obtained from a mammalian membrane preparation and has an apparent molecular weight of about 78 Kilodaltons.

20. A substantially pure mammalian ATP diphosphohydrolase characterized by the following physico chemical properties:
   a catalytic unit of a molecular weight on denaturing polyacrylamide gel electrophoresis of about 78 KDa;
   a deglycosylated form of said catalytic unit of a molecular weight on SDS-PAGE of about 56 Kda.

21. A composition for use in the reduction of platelet aggregation and thrombogenicity comprising as an active ingredient the substantially pure mammalian ATP diphosphohydrolase of claim 20, together with a pharmaceutically acceptable carrier.

22. A composition for converting ATP into ADP and/or ADP into AMP comprising as an active ingredient the substantially pure mammalian ATP diphosphohydrolase of claim 20, together with a pharmaceutically acceptable carrier.

* * * * *

UNITED STATES PATENT AND TRADEMARK OFFICE
CERTIFICATE OF CORRECTION

PATENT NO. : 6,287,837 B1
DATED : September 11, 2001
INVENTOR(S) : Beaudoin et al.

It is certified that error appears in the above-identified patent and that said Letters Patent is hereby corrected as shown below:

<u>Title page,</u>
Item [75], please add inventors, -- Fitz H. Bach and Simon Robson -- to inventors "Adrien R. Beaudoin and Jean Sevigny"

Signed and Sealed this

Second Day of July, 2002

*Attest:*

*Attesting Officer*

JAMES E. ROGAN
*Director of the United States Patent and Trademark Office*

UNITED STATES PATENT AND TRADEMARK OFFICE
CERTIFICATE OF CORRECTION

PATENT NO. : 6,287,837 B1
DATED : September 11, 2003
INVENTOR(S) : Beaudoin et al.

It is certified that error appears in the above-identified patent and that said Letters Patent is hereby corrected as shown below:

Column 20,
Line 38, "herein" should read -- wherein --.
Line 65, "of a" should read -- of a) --.

Signed and Sealed this

Twenty-eighth Day of June, 2005

JON W. DUDAS
*Director of the United States Patent and Trademark Office*

SEQUENCE LISTING

<160> NUMBER OF SEQ ID NOS: 8

<210> SEQ ID NO 1
<211> LENGTH: 510
<212> TYPE: PRT
<213> ORGANISM: Unknown
<220> FEATURE:
<223> OTHER INFORMATION: Description of Unknown Organism: unknown

<400> SEQUENCE: 1

```
Met Glu Asp Thr Lys Glu Ser Asn Val Lys Thr Phe Cys Ser Lys Asn
 1               5                  10                  15

Ile Leu Ala Ile Leu Gly Phe Ser Ser Ile Ala Val Ile Ala Leu
                20                  25                  30

Leu Ala Val Gly Leu Thr Gln Asn Lys Ala Leu Pro Glu Asn Val Lys
                35                  40                  45

Tyr Gly Ile Val Leu Asp Ala Gly Ser Ser His Thr Ser Leu Tyr Ile
                50                  55                  60

Tyr Lys Trp Pro Ala Glu Lys Glu Asn Asp Thr Gly Val Val His Gln
 65                  70                  75                  80

Val Glu Glu Cys Arg Val Lys Gly Pro Gly Ile Ser Lys Phe Val Gln
                85                  90                  95

Lys Val Asn Glu Ile Gly Ile Tyr Leu Thr Asp Cys Met Glu Arg Ala
                100                 105                 110

Arg Glu Val Ile Pro Arg Ser Gln His Gln Glu Thr Pro Val Tyr Leu
                115                 120                 125

Gly Ala Thr Ala Gly Met Arg Leu Leu Arg Met Glu Ser Glu Glu Leu
                130                 135                 140

Ala Asp Arg Val Leu Asp Val Val Glu Arg Ser Leu Ser Asn Tyr Pro
145                 150                 155                 160

Phe Asp Phe Gln Gly Ala Arg Ile Ile Thr Gly Gln Glu Glu Gly Ala
                165                 170                 175

Tyr Gly Trp Ile Thr Ile Asn Tyr Leu Leu Gly Lys Phe Ser Gln Lys
                180                 185                 190

Thr Arg Trp Phe Ser Ile Val Pro Tyr Glu Thr Asn Asn Gln Glu Thr
                195                 200                 205

Phe Gly Ala Leu Asp Leu Gly Gly Ala Ser Thr Gln Val Thr Phe Val
                210                 215                 220

Pro Gln Asn Gln Thr Ile Glu Ser Pro Asp Asn Ala Leu Gln Phe Arg
225                 230                 235                 240

Leu Tyr Gly Lys Asp Tyr Asn Val Tyr Thr His Ser Phe Leu Cys Tyr
                245                 250                 255

Gly Lys Asp Gln Ala Leu Trp Gln Lys Leu Ala Lys Asp Ile Gln Val
                260                 265                 270

Ala Ser Asn Glu Ile Leu Arg Asp Pro Cys Phe His Pro Gly Tyr Lys
                275                 280                 285

Lys Val Val Asn Val Ser Asp Leu Tyr Lys Thr Pro Cys Thr Lys Arg
                290                 295                 300

Phe Glu Met Thr Leu Pro Phe Gln Gln Phe Glu Ile Gln Gly Ile Gly
305                 310                 315                 320

Asn Tyr Gln Gln Cys His Gln Ser Ile Leu Glu Leu Phe Asn Thr Ser
                325                 330                 335

Tyr Cys Pro Tyr Ser Gln Cys Ala Phe Asn Gly Ile Phe Leu Pro Pro
                340                 345                 350
```

```
Leu Gln Gly Asp Phe Gly Ala Phe Ser Ala Phe Tyr Phe Val Met Lys
        355                 360                 365
Phe Leu Asn Leu Thr Ser Glu Lys Val Ser Gln Glu Lys Val Thr Glu
    370                 375                 380
Met Met Lys Lys Phe Cys Ala Gln Pro Trp Glu Glu Ile Lys Thr Ser
385                 390                 395                 400
Tyr Ala Gly Val Lys Glu Lys Tyr Leu Ser Glu Tyr Cys Phe Ser Gly
                405                 410                 415
Thr Tyr Ile Leu Ser Leu Leu Leu Gln Gly Tyr His Phe Thr Ala Asp
                420                 425                 430
Ser Trp Glu His Ile His Phe Ile Gly Lys Ile Gln Gly Ser Asp Ala
        435                 440                 445
Gly Trp Thr Leu Gly Tyr Met Leu Asn Leu Thr Asn Met Ile Pro Ala
        450                 455                 460
Glu Gln Pro Leu Ser Thr Pro Leu Ser His Ser Thr Tyr Val Phe Leu
465                 470                 475                 480
Met Val Leu Phe Ser Leu Val Leu Phe Thr Val Ala Ile Ile Gly Leu
                485                 490                 495
Leu Ile Phe His Lys Pro Ser Tyr Phe Trp Lys Asp Met Val
                500                 505                 510

<210> SEQ ID NO 2
<211> LENGTH: 1818
<212> TYPE: DNA
<213> ORGANISM: Unknown
<220> FEATURE:
<223> OTHER INFORMATION: Description of Unknown Organism: unknown

<400> SEQUENCE: 2
accacaccaa gcagcggctg ggggggggaa agacgaggaa agaggaggaa aacaaaagct      60
gctacttatg gaagatacaa aggagtctaa cgtgaagaca ttttgctcca agaatatcct    120
agccatcctt ggcttctcct ctatcatagc tgtgatagct ttgcttgctg tggggttgac    180
ccagaacaaa gcattgccag aaaacgttaa gtatgggatt gtgctggatg cgggttcttc    240
tcacacaagt ttatacatct ataagtggcc agcagaaaag gagaatgaca caggcgtggt    300
gcatcaagta gaagaatgca gggttaaagg tcctggaatc tcaaaatttg ttcagaaagt    360
aaatgaaata ggcatttacc tgactgattg catggaaaga gctagggaag tgattccaag    420
gtcccagcac caagagacac ccgtttacct gggagccacg gcaggcatgc ggttgctcag    480
gatggaaagt gaagagttgg cagacagggt tctggatgtg gtggagagga gcctcagcaa    540
ctaccccttt gacttccagg gtgccaggat cattactggc caagaggaag gtgcctatgg    600
ctggattact atcaactatc tgctgggcaa attcagtcag aaaacaaggt ggttcagcat    660
agtcccatat gaaaccaata atcaggaaac ctttggagct ttggaccttg gggagcctc    720
tacacaagtc acttttgtac cccaaaacca gactatcgag tccccagata atgctctgca    780
atttcgcctc tatggcaagg actacaatgt ctacacacat agcttcttgt gctatgggaa    840
ggatcaggca ctctggcaga actggccaa ggacattcag gttgcaagta atgaaattct    900
cagggaccca tgctttcatc ctggatataa gaaggtagtg aacgtaagtg accttttacaa    960
gaccccctgc accaagagat ttgagatgac tcttccattc cagcagtttg aaatccaggg   1020
tattggaaac tatcaacaat gccatcaaag catcctggag ctcttcaaca ccagttactg   1080
cccttactcc cagtgtgcct tcaatgggat tttcttgcca ccactccagg gggattttgg   1140
```

-continued

```
ggcattttca gcttttact ttgtgatgaa gttttaaac ttgacatcag agaaagtctc    1200
tcaggaaaag gtgactgaga tgatgaaaaa gttctgtgct cagccttggg aggagataaa    1260
aacatcttac gctggagtaa aggagaagta cctgagtgaa tactgctttt ctggtaccta    1320
cattctctcc ctccttctgc aaggctatca tttcacagct gattcctggg agcacatcca    1380
tttcattggc aagatccagg gcagcgacgc cggctggact ttgggctaca tgctgaacct    1440
gaccaacatg atcccagctg agcaaccatt gtccacacct ctctcccact ccacctatgt    1500
cttcctcatg gttctattct ccctggtcct tttcacagtg gccatcatag gcttgcttat    1560
ctttcacaag ccttcatatt tctggaaaga tatggtatag caaaagcagc tgaaatatgc    1620
tggctggagt gaggaaaaaa tcgtccaggg agcatttcc tccatcgcag tgttcaaggc    1680
catccttccc tgtctgccag ggccagtctt gacgagtgtg aagcttcctt ggcttttact    1740
gaagcctttc ttttggaggt attcaatatc ctttgcctca aggacttcgg cagatactgt    1800
ctctttcatg agttttc                                                   1818
```

<210> SEQ ID NO 3
<211> LENGTH: 11
<212> TYPE: PRT
<213> ORGANISM: Unknown
<220> FEATURE:
<223> OTHER INFORMATION: Description of Unknown Organism: unknown

<400> SEQUENCE: 3

Glu Thr Pro Val Tyr Leu Gly Ala Thr Ala Gly
 1               5                  10

<210> SEQ ID NO 4
<211> LENGTH: 5
<212> TYPE: PRT
<213> ORGANISM: Unknown
<220> FEATURE:
<223> OTHER INFORMATION: Description of Unknown Organism: unknown

<400> SEQUENCE: 4

Leu Leu Arg Met Glu
 1               5

<210> SEQ ID NO 5
<211> LENGTH: 13
<212> TYPE: PRT
<213> ORGANISM: Unknown
<220> FEATURE:
<223> OTHER INFORMATION: Description of Unknown Organism: unknown
<220> FEATURE:
<221> NAME/KEY: UNSURE
<222> LOCATION: (8)

<400> SEQUENCE: 5

Ala Asp Lys Ile Leu Ala Asn Xaa Val Ala Ser Ser Ile
 1               5                  10

<210> SEQ ID NO 6
<211> LENGTH: 10
<212> TYPE: PRT
<213> ORGANISM: Unknown
<220> FEATURE:
<223> OTHER INFORMATION: Description of Unknown Organism: unknown

<400> SEQUENCE: 6

Tyr Pro Phe Asp Phe Gln Gly Ala Arg Ile
 1               5                  10

```
<210> SEQ ID NO 7
<211> LENGTH: 20
<212> TYPE: PRT
<213> ORGANISM: Unknown
<220> FEATURE:
<223> OTHER INFORMATION: Description of Unknown Organism: unknown

<400> SEQUENCE: 7

Lys Ser Asp Thr Gln Glu Thr Tyr Gly Ala Leu Asp Leu Gly Gly Ala
 1               5                  10                  15

Ser Thr Gln Val
            20

<210> SEQ ID NO 8
<211> LENGTH: 16
<212> TYPE: PRT
<213> ORGANISM: Unknown
<220> FEATURE:
<223> OTHER INFORMATION: Description of Unknown Organism: unknown

<400> SEQUENCE: 8

Lys Ser Asp Thr Gln Glu Thr Tyr Gly Ala Leu Asp Leu Gly Gly Ala
 1               5                  10                  15
```